United States Patent
Momose

(10) Patent No.: US 9,274,107 B2
(45) Date of Patent: Mar. 1, 2016

(54) MICROCHIP, MEASUREMENT SYSTEM AND METHOD USING THE SAME, AND TEST REAGENT TO BE USED FOR MICROCHIP

(75) Inventor: Shun Momose, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 386 days.

(21) Appl. No.: 13/474,863

(22) Filed: May 18, 2012

(65) Prior Publication Data
US 2012/0295250 A1    Nov. 22, 2012

(30) Foreign Application Priority Data

May 20, 2011  (JP) ................................. 2011-113587
May 20, 2011  (JP) ................................. 2011-113588

(51) Int. Cl.
| | | |
|---|---|---|
| G01N 33/543 | (2006.01) | |
| G01N 21/03 | (2006.01) | |
| G01N 21/07 | (2006.01) | |

(52) U.S. Cl.
CPC .......... *G01N 33/54386* (2013.01); *G01N 21/03* (2013.01); *G01N 21/07* (2013.01); *G01N 2021/0325* (2013.01); *G01N 2021/0346* (2013.01); *G01N 2333/11* (2013.01)

(58) Field of Classification Search
CPC . G01N 33/54386; G01N 21/07; G01N 21/03; G01N 2021/0346; G01N 2021/0325; G01N 2333/11
See application file for complete search history.

(56) References Cited

U.S. PATENT DOCUMENTS

| | | | |
|---|---|---|---|
| 5,585,278 A | 12/1996 | Vunnam et al. | |
| 6,258,548 B1 * | 7/2001 | Buck | 435/7.1 |
| 2007/0243111 A1 * | 10/2007 | Momose | 422/100 |
| 2009/0142232 A1 * | 6/2009 | Okada et al. | 422/72 |

FOREIGN PATENT DOCUMENTS

| | | |
|---|---|---|
| JP | 8-211060 | 8/1996 |
| JP | 2006-239538 | 9/2006 |
| JP | 2007-225576 | 9/2007 |
| JP | 2009-180688 | 8/2009 |

* cited by examiner

*Primary Examiner* — Lore Jarrett
(74) *Attorney, Agent, or Firm* — Fish & Richardson P.C.

(57) ABSTRACT

A microchip to be used for measuring a plurality of types of objects to be measured. The microchip includes at least a reagent retaining portion and a detecting portion. The test reagent retaining portion includes a plurality of types of test reagents corresponding respectively to the plurality of types of objects to be measured. A plurality of time courses for a change in detected value at the detecting portion caused by a reaction between the test reagents and the objects to be measured corresponding respectively thereto are all different from each other.

11 Claims, 13 Drawing Sheets

MICROCHIP, MEASUREMENT SYSTEM AND METHOD USING THE SAME, AND TEST REAGENT TO BE USED FOR MICROCHIP

BACKGROUND OF THE INVENTION

1. Field of the Invention

The present invention relates to a microchip, measurement system and method using the same, and a test reagent that is used for a microchip. A microchip is used for biochemical tests of DNA, protein, cell, immunity, blood, and the like as well as environmental analysis and chemical synthesis, for example.

2. Description of the Background Art

In recent years, in the fields of medical care, health, food, drug discovery, and the like, detection or quantitation of biological substances such as DNA (Deoxyribo Nucleic Acid), enzyme, antigen, antibody, protein, virus, and cell as well as chemical substances has become increasingly important, and various biochips and micro chemical chips (such chips will hereinafter be collectively referred to as microchip) with which the above-described substances can be easily and conveniently measured have been proposed.

The microchip can be used to allow a series of experimental and analytical operations usually performed in a laboratory to be conducted within the chip of several centimeters to 10 centimeters per side and approximately several millimeters to several centimeters in thickness. The microchip accordingly provides many advantages that the amounts of samples and reagents to be used are very small, the cost is low, the reaction rate is high, high throughput test or analysis can be conducted, and the test results can be immediately obtained at the site where the sample was taken, for example.

The microchip has a fluid circuit therein. The fluid circuit is mainly constituted of: portions including, for example, a reagent retaining portion for retaining a test reagent to be mixed or reacted with a sample (such as blood) to be tested or analyzed or to treat the sample, a measuring portion for measuring the sample and/or test reagent, a mixing portion for mixing the sample and the test reagent together, and a detecting portion for testing or analyzing the liquid mixture; and a fine fluid channel appropriately connecting these portions. For use, the microchip is mounted typically in a device that can apply a centrifugal force thereto. By applying a centrifugal force in an appropriate direction to the microchip, treatments such as measurement of a sample (or a specific component in the sample) and/or a test reagent, mixing of the sample (or a specific component in the sample) and the test reagent together, and introduction of the obtained liquid mixture into the detecting portion can be performed. It is noted that treatments of various fluids (such as a sample, a specific component in the sample, a test reagent, or a mixture or a reactant of two or more types thereof) performed in the microchip, such as transfer from a portion to any other portion, measurement, and mixing of the fluids will hereinafter sometimes be referred to as "fluid treatment".

Various microchips including such a fluid circuit have been disclosed (see for example Japanese Patent Laying-Open No. 2006-239538). However, in a measurement method using such a conventional microchip, one detecting portion (optical cell) has been able to perform measurement on only one test item. Thus, in order to perform measurement on a plurality of test items, a plurality of optical cells (cuvettes), optical systems, and the likes have been required.

In addition, in such a case where a fluid treatment is performed by application of a centrifugal force, when a metal colloid reagent is used as a test reagent, since metal has a specific gravity (e.g., Au: 19.3, Pt: 21.45, Ag: 10.49) that is greater than the water's specific gravity of 1, application of a centrifugal force in the fluid treatment may cause metal 5 to separate in a liquid mixture 31 containing a gold colloid reagent, as shown in FIG. 14.

SUMMARY OF THE INVENTION

An object of the present invention is to provide a microchip in which one detecting unit can perform measurement of a plurality of types of objects to be measured (tests on a plurality of items) as well as measurement system and method using the microchip.

Another object of the present invention is to provide a test reagent that is composed of a liquid dispersion and not likely to exhibit separation of a dispersoid even when a centrifugal force is applied to a microchip.

The present invention is a microchip to be used for measuring a plurality of types of objects to be measured, the microchip including at least: a reagent retaining portion; and a detecting portion. The reagent retaining portion includes a plurality of types of test reagents corresponding respectively to the plurality of types of objects to be measured. A plurality of time courses for a change in detected value at the detecting portion caused by a reaction between the test reagents and the objects to be measured corresponding respectively thereto are all different from each other. Preferably, the microchip includes only one such detecting portion.

Preferably, the plurality of time courses include both a positive time course indicating the tendency of an increase in the detected value over time and a negative time course indicating the tendency of a decrease in the detected value over time.

Preferably, all of the plurality of time courses are time courses adapted to a rate assay in which the object to be measured is detected based on the rate of change in the detected value at the elapse of a predetermined period of time.

Preferably, the plurality of time courses include both a time course adapted to a rate assay in which the object to be measured is detected based on the rate of change in the detected value at the elapse of a predetermined period of time and a time course adapted to an end-point assay in which the object to be measured is detected based on an amount of change in the detected value at the elapse of a predetermined period of time relative to an initial value of the detected value.

Preferably, the plurality of types of test reagents include at least one type of latex reagent and at least one type of gold colloid reagent.

Preferably, the plurality of types of objects to be measured are an influenza A virus and an influenza B virus, and the plurality of types of test reagents are a latex reagent and a gold colloid reagent.

Preferably, the detected value is detected through optical measurement using a plurality of wavelengths.

Preferably, the microchip of the present invention is used for point of care testing. Further, the present invention also relates to a measurement system using the above-described microchip.

Further, the present invention also relates to a measurement method for measuring a plurality of types of objects to be measured using a microchip. The microchip includes at least: a reagent retaining portion; and a detecting portion. The reagent retaining portion includes a plurality of types of test reagents corresponding respectively to the plurality of types of objects to be measured. A plurality of time courses for a change in detected value at the detecting portion caused by a reaction between the test reagents and the objects to be measured corresponding respectively thereto are all different from each other.

Preferably, the detected value is detected through optical measurement using a plurality of wavelengths.

Further, the present invention also relates to a test reagent to be used for a microchip for measuring an object to be measured. The test reagent is composed of a liquid dispersion containing, as a dispersoid, a composite particle including a core particle and a metal layer covering a surface of said core particle. The composite particle has a specific gravity of not more than 10.

Preferably, the core particle is composed of a material having a specific gravity of 0.8 to 1.2. Further, preferably, the core particle is composed of a resin. Still further, preferably, the liquid dispersion is a liquid colloidal dispersion.

Preferably, the metal layer has a surface on which a molecule having a property of binding specifically to the object to be measured is immobilized.

Preferably, the microchip has a structure for transferring at least the object to be measured and the test reagent from a portion to any other portion by utilizing a centrifugal force.

In measurement using the microchip of the present invention, since every pattern of a time course of a detected value for each of objects to be measured is different, one detecting portion can perform measurement of a plurality of objects to be measured. Even when a test is to be conducted on a plurality of items, it is not necessarily required to provide a plurality of optical cells; therefore, the microchip and/or the measurement system using the same can be simplified in structure. Since one detecting portion can perform measurement for a plurality items, an amount of sample required for measurement can be reduced.

The test reagent of the present invention can provide a test reagent that is composed of a liquid dispersion and not likely to exhibit separation of a dispersoid even when a centrifugal force is applied to a microchip while maintaining a property as a test reagent.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
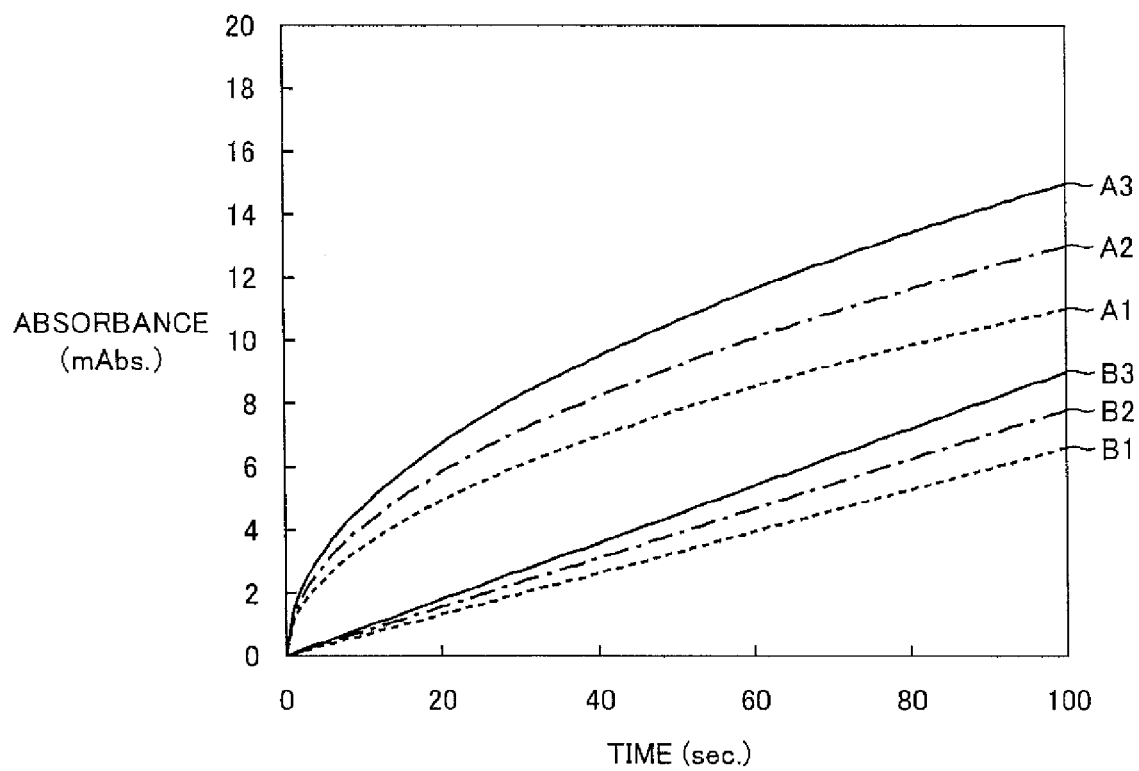
FIG. 1 is a schematic graph for illustrating a measurement method in a first embodiment.

A microchip of the present invention is a microchip with which various types of chemical syntheses, tests, and analyses for example can be performed by means of a fluid circuit of the microchip. The size of the microchip is not particularly limited to a specific one, and may be approximately several centimeters to 10 centimeters in length and width each and approximately several millimeters to several centimeters in thickness.

The microchip is constituted of, for example, a first substrate having, at least in its one surface, a concave portion sectioned by a partition and a second substrate bonded to at least the one surface of the first substrate. The fluid circuit of the microchip includes space defined by the concave portion and the surface of the second substrate.

Further, the microchip may be constituted of three or more layers of substrates. For instance, the first substrate may have a further concave portion also in a surface on the side opposite to the second substrate, and a third substrate similar to the second substrate may be bonded to the further-concave-portion-side of the first substrate. In this case, the fluid circuit is structured to include two layers of fluid circuits, namely, a first fluid circuit that is composed of space defined by the concave portion provided in the second-substrate-side surface of the first substrate and the surface of the second substrate and a second fluid circuit that is composed of space defined by the concave portion provided in the third-substrate-side surface of the first substrate and the surface of the third substrate. Here, "two layers" means that the fluid circuits are provided respectively at two positions that are different in the thickness direction of the microchip. Such two layers of fluid circuits can be connected together by a through hole extending through the first substrate in the thickness direction.

The method for bonding the substrates together is not particularly limited to a specific one, and examples of the method include: a method for welding the substrates together by melting a to-be-bonded surface of at least one of the substrates to be bonded to each other (welding method); and a method for joining the substrates together by means of an adhesive. Examples of the welding method include: a method for welding the substrates together by heating the substrates; a method for welding the substrates together by means of heat generated when the light such as a laser is absorbed (laser welding); and a method for welding the substrates together by means of ultrasonic waves.

The material for each of the substrates constituting the microchip in the present embodiment is not particularly limited to a specific one, and may be for example any of organic materials such as polyethylene terephthalate (PET), polyethylene naphthalate (PEN), polybutylene terephthalate (PBT), polymethylmethacrylate (PMMA), polycarbonate (PC), polystyrene (PS), polypropylene (PP), polyethylene (PE), polyarylate (PAR) resin, acrylonitrile-butadiene-styrene (ABS) resin, styrene-butadiene resin (styrene-butadiene copolymer), polyvinyl chloride (PVC) resin, polymethylpentene (PMP) resin, polybutadiene (PBD) resin, biodegradable polymer (BP), cycloolefin polymer (COP), polydimethylsiloxane (PDMS), polyacetal (POM), and polyamide (PA) and inorganic materials such as silicon, glass, and quartz. Especially, it is preferable to use a resin in consideration of the ease with which the fluid circuit can be formed, for example.

The method for forming a concave portion (pattern groove) and a partition by which the fluid circuit is constituted in the surface of the first substrate is not particularly limited to a specific one, and examples of the method include an injection molding method using a mold having a transfer structure and an imprinting method. The shapes of the concave portion and the partition are determined to provide an appropriate fluid circuit structure.

In the microchip, the fluid circuit includes various portions disposed at appropriate positions in the fluid circuit so that appropriate fluid treatments can be performed on the fluid (such as a sample, a specific component in the sample, a test reagent, and a liquid mixture or a liquid reactant of two or more types thereof) in the fluid circuit, and these portions are appropriately connected via a fine flow channel (connection channel). Examples of the portions in the fluid circuit include: a reagent retaining portion for retaining a test reagent; a mixing portion for mixing a sample and the test reagent together; and a detecting portion for testing or analyzing the obtained liquid mixture (for example, detection of a specific component in the liquid mixture). The microchip of the present invention includes at least the reagent retaining portion and the detecting portion. It is preferable that one microchip has one detecting portion therein.

"Sample" herein refers to a substance to be introduced into the fluid circuit and to be subjected to a test, an analysis or the like performed by the microchip, and examples thereof include whole blood, blood plasma, blood serum, urine, a nasal swab, a nasal aspirate, a self-blown nasal discharge, and a throat swab. "Test reagent" refers to a reagent that treats a sample to be subjected to a test or an analysis performed by the microchip or is mixed or reacted with the sample, and usually contained in advance within the reagent retaining portion of the fluid circuit prior to the use of the microchip. It is preferable that at least any one of a sample and a test reagent is a liquid. The liquid mixture or liquid reactant finally obtained by mixing a sample with a test reagent undergoes optical measurement or the like, for example, detecting the intensity (transmittance) of the light applied to and transmitted through the detecting portion that contains the liquid mixture, measuring the absorption spectrum of the liquid mixture retained in the detecting portion, and the like and the liquid mixture or liquid reactant is accordingly tested and analyzed.

Various fluid treatments to be performed in the fluid circuit, such as mixing of a sample with a test reagent and introduction of the resultant liquid mixture into the detecting portion can be carried out for example by successively applying a centrifugal force in an appropriate direction to the microchip. The centrifugal force can be applied to the microchip mounted on an apparatus (centrifugal apparatus) capable of applying a centrifugal force. The centrifugal apparatus usually includes a freely rotatable rotor (rotating body) and a freely rotatable stage placed on the rotor. The microchip is mounted on the stage and the stage is rotated to set the angle of the microchip with respect to the rotor to an arbitrary angle, so that the centrifugal force in an arbitrary direction can be applied to the microchip.

The liquid mixture finally obtained by mixing a sample with a test reagent undergoes optical measurement or the like, for example, detecting the intensity (transmittance) of the light applied to and transmitted through the detecting portion that contains the liquid mixture, measuring the absorption spectrum of the liquid mixture retained in the detecting portion, and the like, and the liquid mixture or liquid reactant is accordingly tested and analyzed.

The microchip of the present invention is a microchip to be used for measuring a plurality of types of objects to be measured, and the reagent retaining portion includes a plurality of types of test reagents corresponding respectively to the plurality of types of objects to be measured. The plurality of types of test reagents are selected such that a plurality of time courses for a change in detected value at the detecting portion caused by a reaction between the test reagents and the object to be measured corresponding respectively thereto are all different from each other. The time course herein means the manner of change in detected value over time.

The plurality of types of test reagents may be contained within one test reagent retaining portion retaining a liquid mixture or the like of the plurality of types of test reagents or may be contained within separate test reagent retaining portions retaining each of the rest reagents.

The microchip and the measurement system using the same of the present invention can be suitably used particularly for Point Of Care Testing (POCT). The POCT is a real time testing carried out in clinical practice with the use of a small analyzer and/or a rapid diagnostic kit. Examples of the POCT include tests for infectious diseases such as an influenza virus test and an adenovirus test, a test for troponin T to confirm whether or not any myocardial infarction or myocardial injury is present, a test for blood gas and/or a blood cell count for understanding the general status, and a test for electrolytes and/or blood glucose.

The present invention also relates to a test reagent to be used for such a microchip for measuring an object to be measured. The test reagent of the present invention is composed of a liquid dispersion containing, as a dispersoid, a composite particle including a core particle and a metal layer covering the surface of the core particle. The composite particle has a specific gravity of not more than 10. The composite particle has a specific gravity of preferably not more than 5 and more preferably not more than 2.

It is preferable that the core particle is composed of a material having a specific gravity of 0.8 to 1.2. This allows the particle to serve as a dispersoid to have a less specific gravity than that of a particle composed only of metal.

It is also preferable that the core particle is composed of a resin. A core particle composed of a resin can be readily controlled in particle size through various publicly-known methods and therefore enables fabrication of a metal coating dispersoid of a size that is most appropriate for measurement, thereby making it possible to provide enhanced measurement sensitivity. Examples of the resin include polyethylene (PE), polypropylene (PP), polystyrene (PS), an ABS resin, an AS resin, polycarbonate (PC), polyethylene terephthalate (PET), and polymethylpentene (PMP).

It is preferable that the metal layer is a sufficiently thin layer relative to the diameter of the core particle. The metal layer made sufficiently thin allows the whole particle to serve as a dispersoid to have a relative gravity of close to 1, and therefore it is possible to suppress separation of the test reagent upon application of centrifugal force. The metal layer has a thickness of preferably not more than 10% of the diameter of the core particle, more preferably not more than 3%, and further preferably not more than 1%. Specifically, the metal layer has a thickness of preferably 0.3 to 100 nm and more preferably 1 to 5 nm. Examples of the metal layer include gold, platinum, and silver.

It is preferable that the liquid dispersion is a liquid colloidal dispersion. In the present invention, the liquid colloidal dispersion refers to a liquid dispersion that contains, as a dispersoid, a particle having a diameter of 1 to 1000 nm.

It is preferable that the metal layer has a surface on which a molecule having a property of binding specifically to the object to be measured is immobilized. Examples of a combination of a molecule having a property of binding specifically to an object to be measured and the object to be measured include an antibody and an antigen, a sugar chain and a protein, a lipid and a protein, a ligand (low-molecular compound) and a protein, a protein and a protein, and a single-stranded DNA and a single-stranded DNA.

It is preferable that the microchip above has a structure for transferring at least the object to be measured and the test reagent from a portion to any other portion by utilizing a centrifugal force.

The present invention will be hereinafter described in detail with illustration of embodiments.

First Embodiment

FIG. 1 is a schematic graph for illustrating a measurement method in a first embodiment.

In FIG. 1, A1 to A3 are schematic graphs each indicating a time course of absorbance (detected value) for a liquid mixture of a sample containing an object to be measured A and a test reagent 1. A1, A2 and A3 are in ascending order of the concentrations of object to be measured A in the samples. These time courses are positive time courses that indicate the tendency of an increase in detected value over time.

B1 to B3 are schematic graphs each indicating a time course of absorbance (detected value) for a liquid mixture of a sample containing an object to be measured B and a test reagent 2. B1, B2 and B3 are in ascending order of the concentrations of object to be measured B in the samples. These time courses are also positive time courses that indicate the tendency of an increase in detected value over time.

In other words, in the present embodiment, test reagents 1 and 2 are selected such that a plurality of time courses for a change in detected value at the detecting portion caused by a reaction between test reagents 1, 2 and objects to be measured A, B corresponding respectively thereto are all different from each other.

In the present embodiment, test reagents 1, 2 are selected such that all of their respective time courses are positive time courses. However, in the present invention, all of the plurality of time courses may be positive time courses or negative time courses in this manner, or the plurality of time courses may include both a positive time course and a negative time course as in a second embodiment that will be described later.

In the present embodiment, the reaction is slow both in a reaction between object to be measured A and test reagent 1 and in a reaction between object to be measured B and test reagent 2. Therefore, the time courses for A1 to A3 and the time courses for B1 to B3 are all time courses adapted to a rate assay in which an object to be measured is detected based on the rate of change in detected value at the elapse of a predetermined period of time.

The use of a microchip including such plurality of types of test reagents in the test reagent retaining portion makes it possible to detect which of objects to be measured A and B is contained in a sample from the difference between the time courses for test reagents 1 and 2. In addition, if once measurements such as A1 to A3 and B1 to B3 in FIG. 1 are obtained in advance through preliminary measurement and a calibration curve is prepared based on the measurements, it is also possible to measure the concentrations of objects to be measured A and B, for example. It is noted that the present embodiment is suitably used when the sample is one that usually includes only any one of objects to be measured A and B.

Second Embodiment

Figure 2:
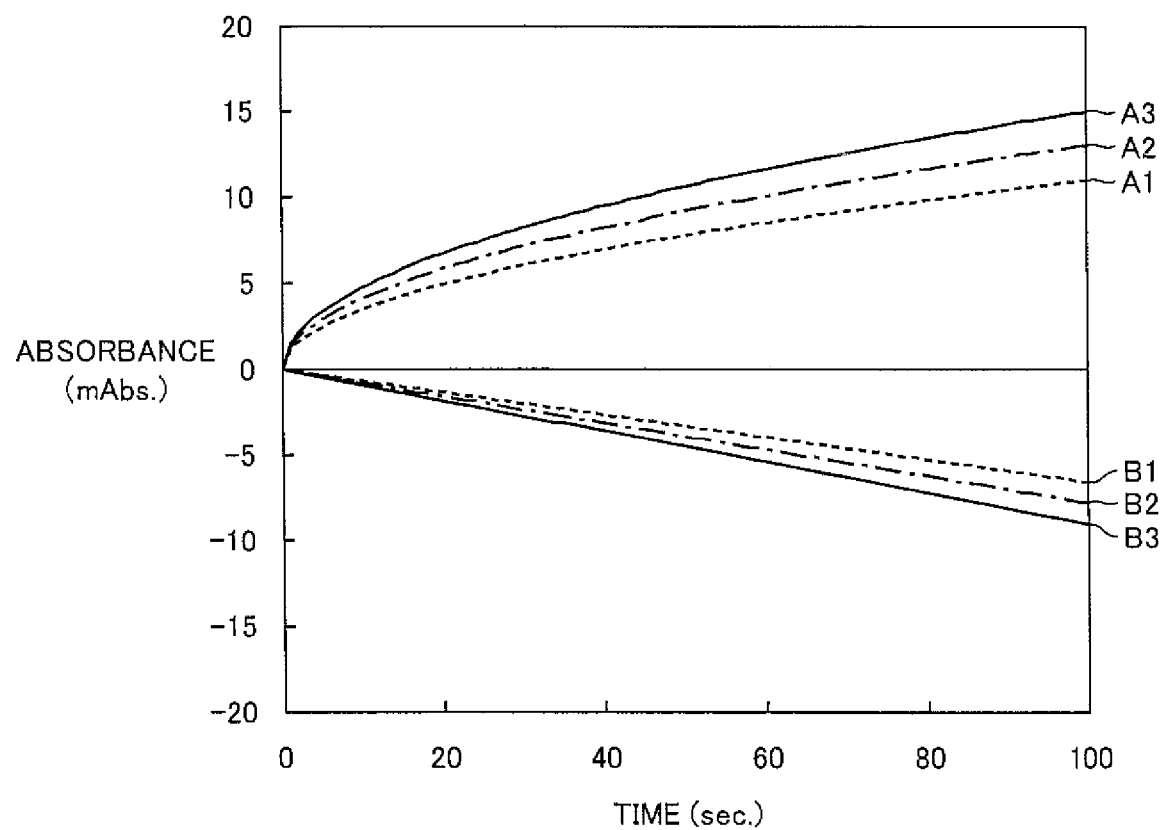
FIG. 2 is a schematic graph for illustrating a measurement method in a second embodiment.

FIG. 2 is a schematic graph for illustrating a measurement method in a second embodiment.

In FIG. 2, A1 to A3 are schematic graphs each indicating a time course of absorbance (detected value) for a liquid mixture of a sample containing object to be measured A and test reagent 1. A1, A2 and A3 are in ascending order of the concentrations of object to be measured A in the samples. These time courses are positive time courses that indicate the tendency of an increase in detected value over time.

In contrast, B1 to B3 are schematic graphs each indicating a time course of absorbance (detected value) for a liquid mixture of a sample containing object to be measured B and test reagent 2. B1, B2 and B3 are in ascending order of the concentrations of object to be measured B in the samples. These time courses are negative time courses that indicate that the tendency of a decrease in detected value over time.

In other words, in the present embodiment, test reagents 1 and 2 are selected such that a plurality of time courses for a change in detected value at the detecting portion caused by a reaction between test reagents 1, 2 and objects to be measured A, B corresponding respectively thereto are all different from each other. Test reagents 1 and 2 are also selected such that the plurality of time courses include both a positive time course and a negative time course. Usually, each of such time courses can be achieved by selecting the type of the test reagent.

It is noted that in the present embodiment, the reaction is slow both in a reaction between object to be measured A and test reagent 1 and in a reaction between object to be measured B and test reagent 2. Therefore, the time courses for A1 to A3 and the time courses for B1 to B3 are all time courses adapted to a rate assay in which an object to be measured is detected based on the rate of change in detected value at the elapse of a predetermined period of time.

The use of a microchip including such plurality of types of test reagents in the test reagent retaining portion makes it possible to detect which of objects to be measured A and B is contained in a sample from the difference between the time courses for test reagents 1 and 2. Particularly, in the present embodiment, since the time courses for test reagents 1 and 2 are positive and negative time courses, respectively, it is possible to determine which of objects to be measured A and B is contained in a sample depending solely on whether a time course in a detection result is positive or negative. In addition, if once measurements such as A1 to A3 and B1 to B3 in FIG. 1 are obtained in advance through preliminary measurement and a calibration curve is prepared based on the measurements, it is also possible to measure the concentrations of objects to be measured A and B, for example. It is noted that the present embodiment is suitably used when the sample is one that usually includes only any one of objects to be measured A and B.

Third Embodiment

Figure 3:
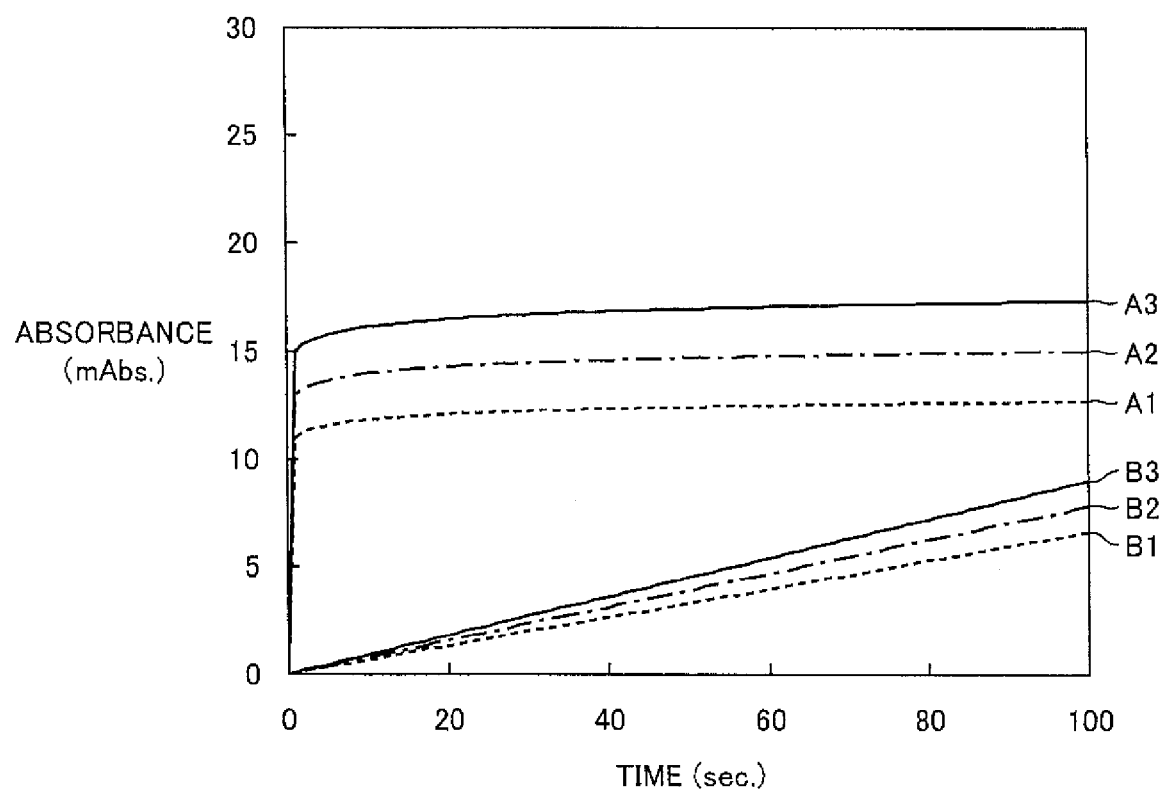
FIG. 3 is a schematic graph for illustrating a measurement method in a third embodiment.

FIG. 3 is a schematic graph for illustrating a measurement method in a third embodiment.

In FIG. 3, A1 to A3 are schematic graphs each indicating a time course of absorbance (detected value) for a liquid mixture of a sample containing object to be measured A and test reagent 1. A1, A2 and A3 are in ascending order of the concentrations of object to be measured A in the samples. These time courses are positive time courses that indicate the tendency of an increase in detected value over time. Object to be measured A and test reagent 1 reacts with each other at a high rate, and the absorbance (detected value) enters an approximately steady state at the initial stage. Therefore, the time courses for A1 to A3 are time courses adapted to an end-point assay in which an object to be measured is detected based on an amount of change in detected value at the elapse of a predetermined period of time relative to the initial value of the detected value.

B1 to B3 are schematic graphs each indicating a time course of absorbance (detected value) for a liquid mixture of a sample containing object to be measured B and test reagent 2. B1, B2 and B3 are in ascending order of the concentrations of object to be measured B in the samples. These time courses are also positive time courses that indicate the tendency of an increase in detected value over time. The reaction between object to be measured B and test reagent 2 is slow. Therefore, the time courses for B1 to B3 are adapted to a rate assay in which an object to be measured is detected based on the rate of change in detected value at the elapse of a predetermined period of time.

In other words, in the present embodiment, although both test reagents 1 and 2 have a positive time course for a change in detected value at the detecting portion caused by a reaction between test reagents 1, 2 and objects to be measured A, B corresponding respectively thereto, one has a time course adapted to an end-point assay and the other has a time course adapted to a rate assay. Usually, each of such time courses can be achieved by selecting the type of the test reagent.

The use of a microchip including such plurality of types of test reagents in the test reagent retaining portion facilitates determination of an object to be measured contained in a sample even when all of the time courses for test reagents are positive (or negative) time courses. In addition, if once measurements such as A1 to A3 and B1 to B3 in FIG. 3 are obtained in advance through preliminary measurement and a calibration curve is prepared based on the measurements, it is also possible to measure the concentrations of objects to be measured A and B, for example.

EXAMPLES

Example 1

An outline of an fluid treatment using a microchip 1 of the present example will be described with reference to FIG. 4(a)-(d). FIG. 4(a)-(d) is a schematic top view of a microchip in each step of a measurement method of Example 1.

(1) Mixing Step

Figure 4:
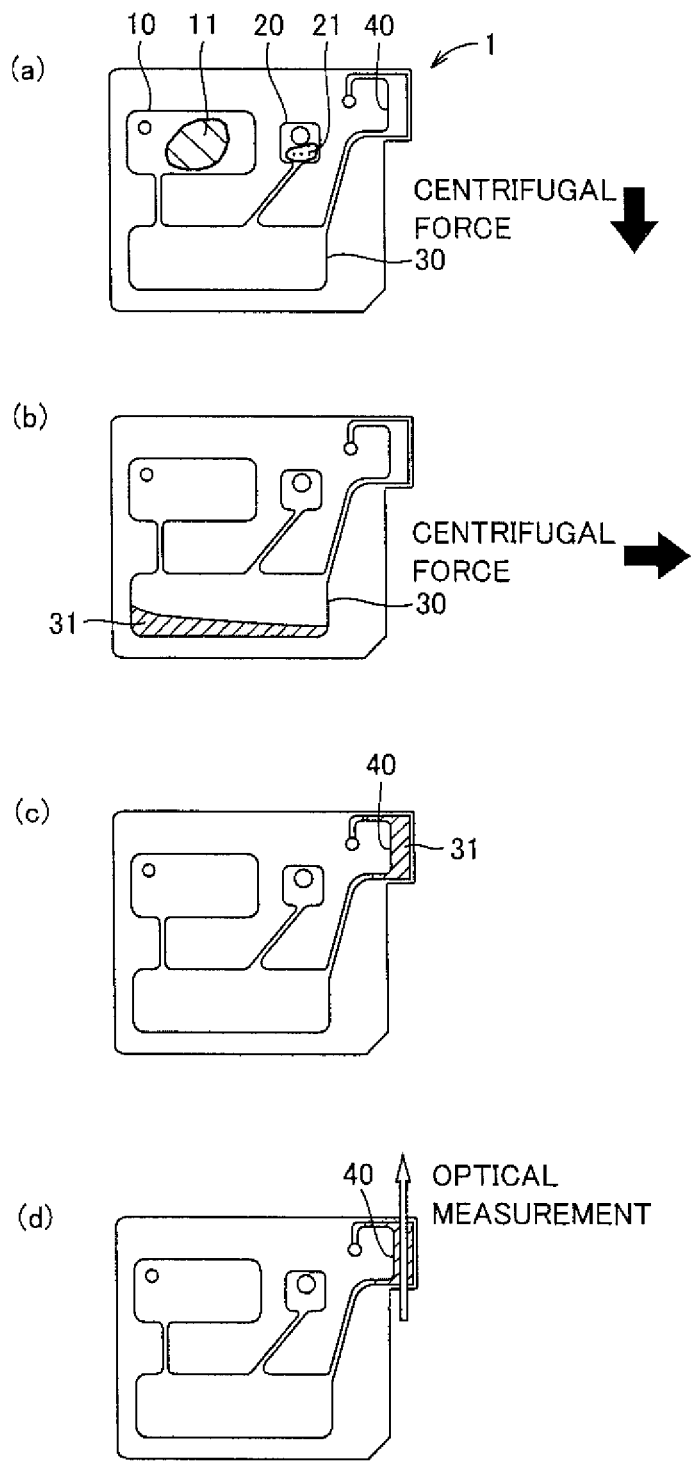
FIG. 4(a)-(d) is a schematic top view of a microchip in each step of a measurement method of Example 1.

First, a centrifugal force is applied downward (in the direction of an arrow in FIG. 4(a)) to microchip 1 in a state as shown in FIG. 4(a). A test reagent 11 that has been contained within a test reagent retaining portion 10 and a sample 21 that has been introduced into a sample retaining portion 20 are thereby introduced into a mixing portion 30 and produce a liquid mixture 31 (FIG. 4(b)). It is noted that test reagent 11 is a liquid mixture of a latex reagent on which an influenza A virus antibody is immobilized and a gold colloid reagent on which an influenza B virus antibody is immobilized.

(2) Introduction into Detecting Portion Step

Next, a centrifugal force is applied rightward (in the direction of an arrow in FIG. 4(b)). Liquid mixture 31 is thereby introduced into a detecting portion 40 through a connecting flow channel (FIG. 4(c)).

(3) Detection Step

Liquid mixture 31 that has been filled into the detecting portion undergoes optical measurement and is accordingly tested and/or analyzed. For instance, by applying light from the direction of an arrow shown in FIG. 4(d) and measuring the transmitted light, detection of a specific component in the liquid mixture, for example, is performed.

Samples used in the present example were nasal discharges (liquids discharged by blowing one's nose) collected from an affected individual who is influenza A positive and an affected individual who is influenza B positive, respectively, and a liquid mixture of equal parts of both of the nasal discharges. As a control, a nasal discharge collected from a healthy individual who is influenza A and B negative was also used.

As a test reagent for an object to be measured, an influenza A virus, a latex reagent on which an influenza A virus antibody was immobilized was used. As a test reagent for an influenza B virus, a gold colloid reagent on which an influenza B virus antibody was immobilized was used. The light used for measurement was of a wavelength of 505 nm, and each sample was measured for three times.

Figure 5:
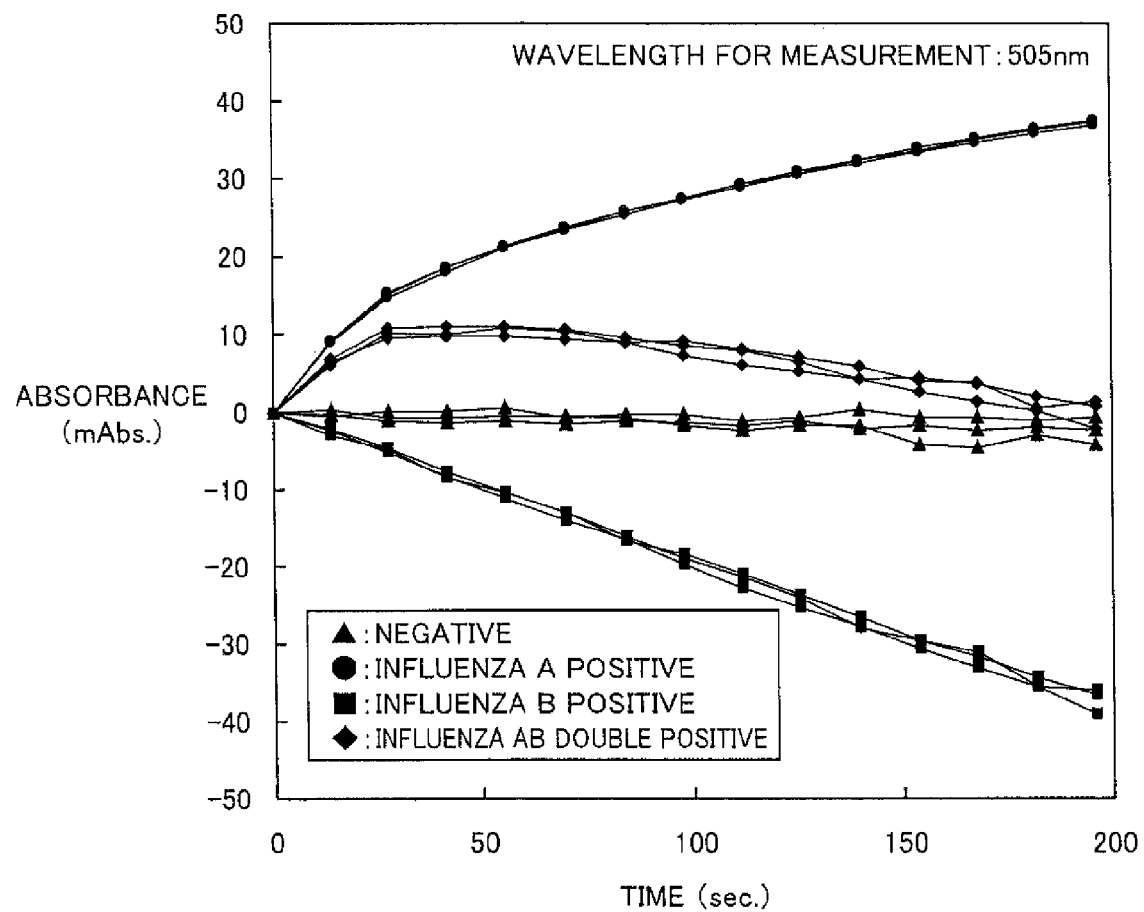
FIG. 5 is a graph showing measurements in Example 1.

FIG. 5 is a graph showing measurements in Example 1. It is noted that FIG. 5 displays all measurements over one another. As can be seen from FIG. 5, all of influenza A positive, influenza B positive, double positive, and double negative can be determined from the time courses of absorbance. Here, the time courses for the influenza A positive sample are positive time courses, while the time courses for the influenza B positive sample are negative time courses. Although it is considered that unusually an individual is not affected by both of influenza A and influenza B (double positive), in consideration of a double positive case, measurement was also performed on the liquid mixture of equal parts of the nasal discharge from the influenza A affected individual and the nasal discharge from the influenza B affected individual. As shown in FIG. 5, the time courses of the double positive sample have a feature that the rate of change in absorption changes from positive to negative. In contrast, the time courses of samples that are each either influenza A positive or influenza B positive have a feature that the rate of change in absorption is always positive or always negative. It is possible to determine the double positive sample and the samples that are each either influenza A positive or influenza B positive, based on this difference in time course.

Example 2

Figure 6:
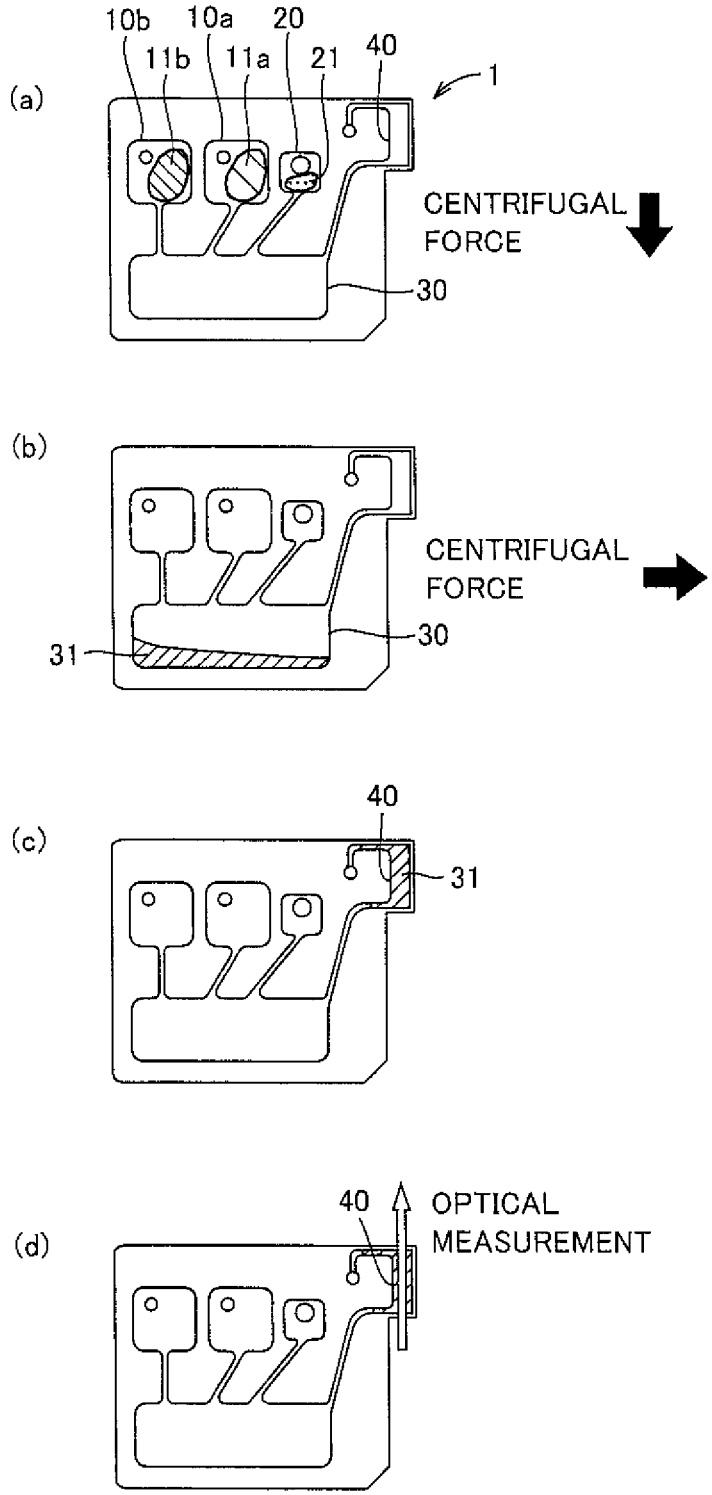
FIG. 6(a)-(d) is a schematic top view of a microchip in each step of a measurement method of Example 2.

FIG. 6(a)-(d) is a schematic top view of a microchip in each step of a measurement method of Example 2. In the present example, as shown in FIG. 6(a), test reagents 11a, 11b are contained in separate test reagent retaining portions 10a, 10b. The present example is otherwise the same as Example 1, and therefore a description thereof will not be repeated. Such a configuration is effective when it is necessary to retain a plurality of types of test reagents separately up until the point of measurement.

Example 3

In the present example, optical measurement at the detecting portion was performed using two wavelengths of 450 nm and 505 nm, respectively. The measurement was performed on an influenza A positive sample (a nasal discharge from an influenza A affected individual), an influenza B positive sample (a nasal discharge from an influenza B affected individual), and a negative sample (a nasal discharge from a healthy individual). The present example is otherwise the same as Example 1, and therefore a description thereof will not be repeated.

Figure 7:
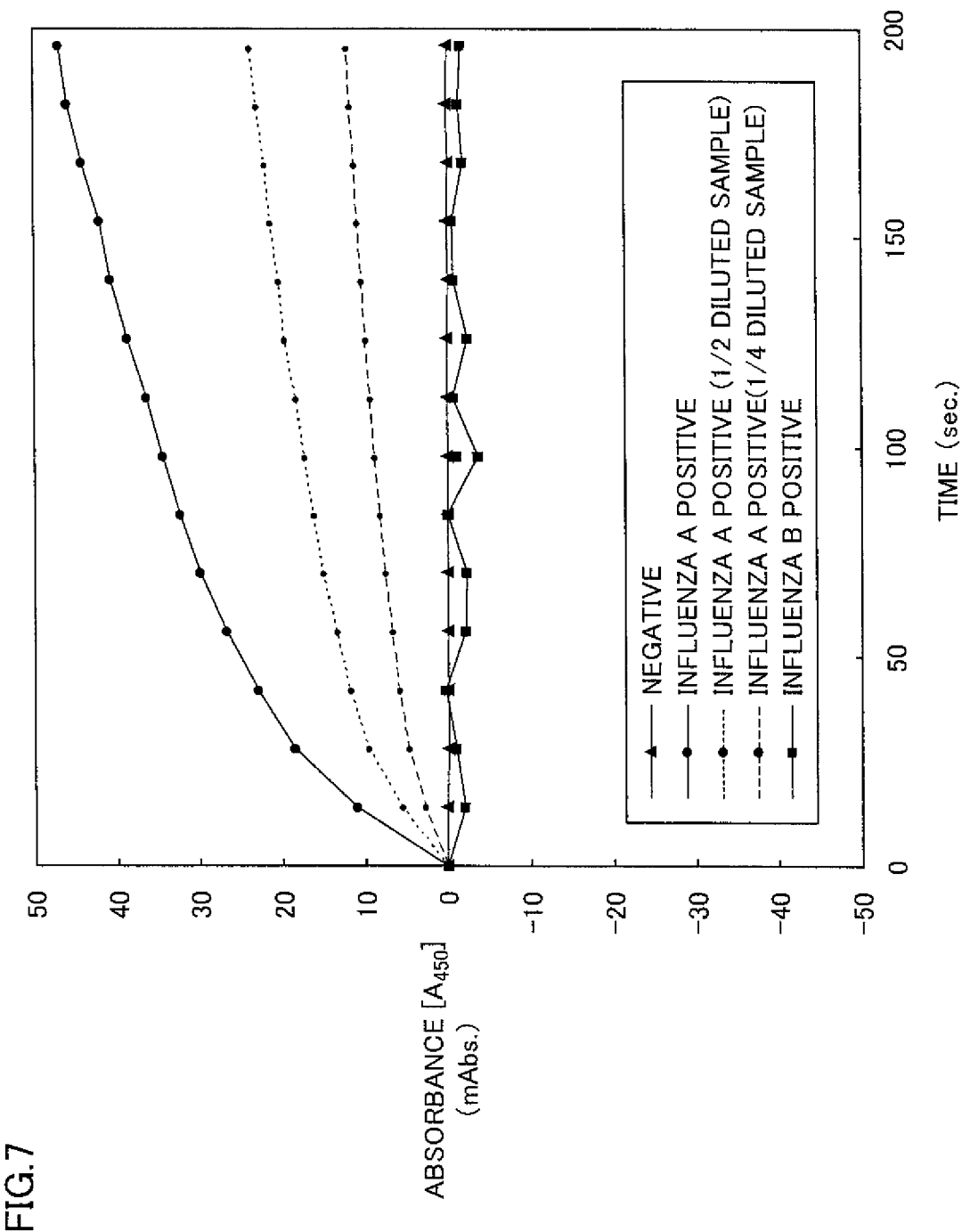
FIG. 7 is a graph showing measurements in Example 3.

FIG. 7 is a graph of the absorbance for 450 nm wavelength light ($A_{450}$). It is noted that as to the influenza A positive sample, measurements for a ½ diluted solution and a ¼ diluted solution are also shown. It can be seen from FIG. 7 that the optical measurement using 450 nm wavelength light allows measurement of an influenza A virus alone.

Figure 8:
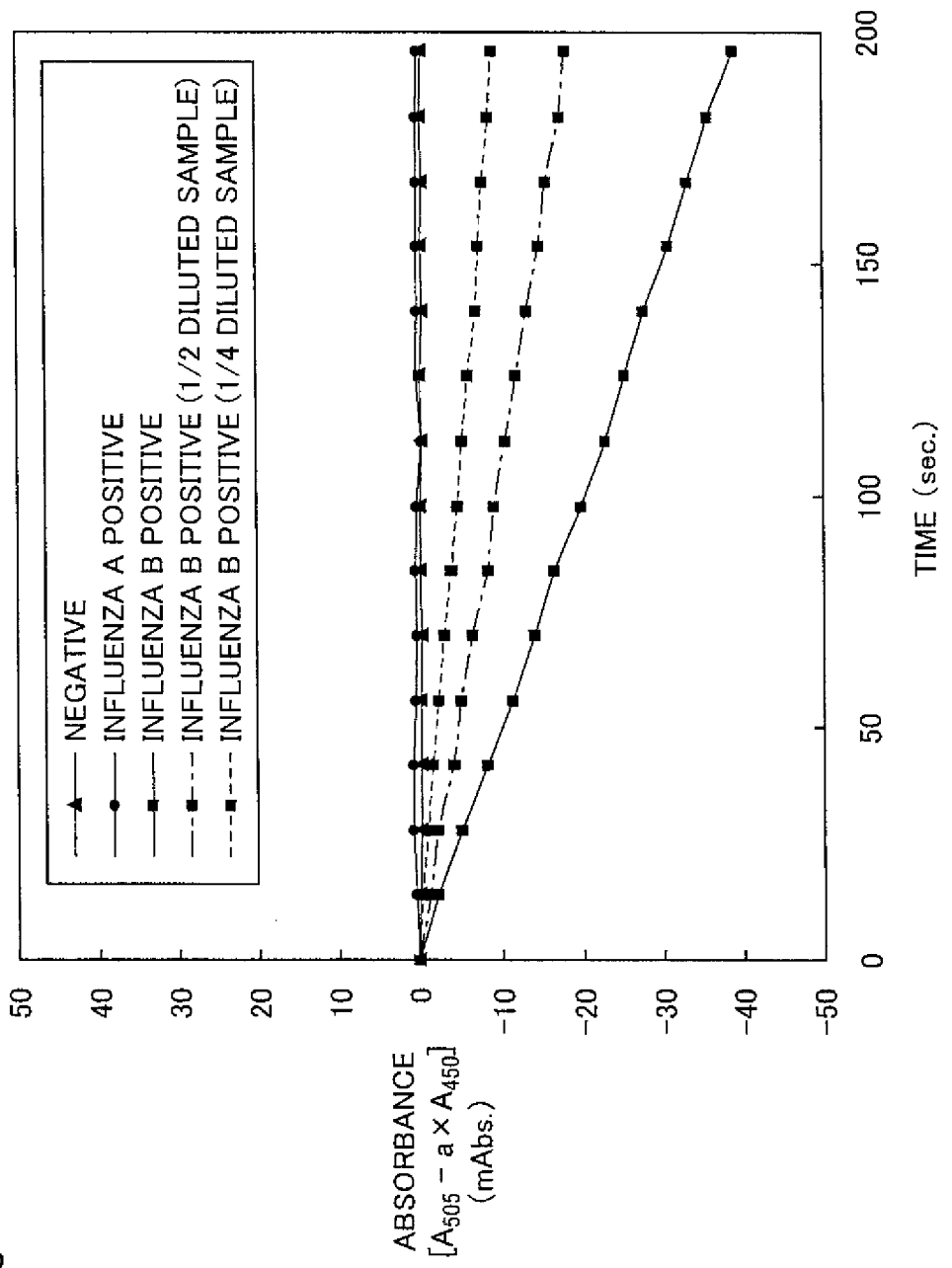
FIG. 8 is a graph showing another set of measurements in Example 3.

On the other hand, FIG. 8 is a graph of values ($A_{505}$–a× $A_{450}$) which are obtained by subtracting the absorbance for 450 nm wavelength light ($A_{450}$) multiplied by a (constant) from the absorbance for 505 nm wavelength light. Here, the constant a is 0.79. This constant a is the ratio of the absorbance for 505 nm wavelength light to the absorbance for 450 nm wavelength light as to a liquid reactant of the latex reagent and an influenza A virus, which is an inherent value of the latex reagent. The ratio a is constant regardless of a change in the concentration of an influenza virus. It is noted that as to the influenza B positive sample, measurements for a ½ diluted solution and a ¼ diluted solution are also shown. It can be seen from FIG. 8 that the optical measurement using 450 nm wavelength light and 505 nm wavelength light allows measurement of an influenza B virus alone. In this way, when measurement is performed using a plurality of wavelengths, it is possible to separate individual measurements (individual time courses) from the overall measurements (the time course synthesized from the individual time courses) to examine the concentration of an object to be measured, for example.

Example 4

An outline of an fluid treatment using microchip 1 of the present example will be described with reference to FIG. 9(a)-(e). FIG. 9(a)-(e) is a schematic top view of a microchip in each step of a measurement method of Example 4.

(1) First Mixing Step

Figure 9:
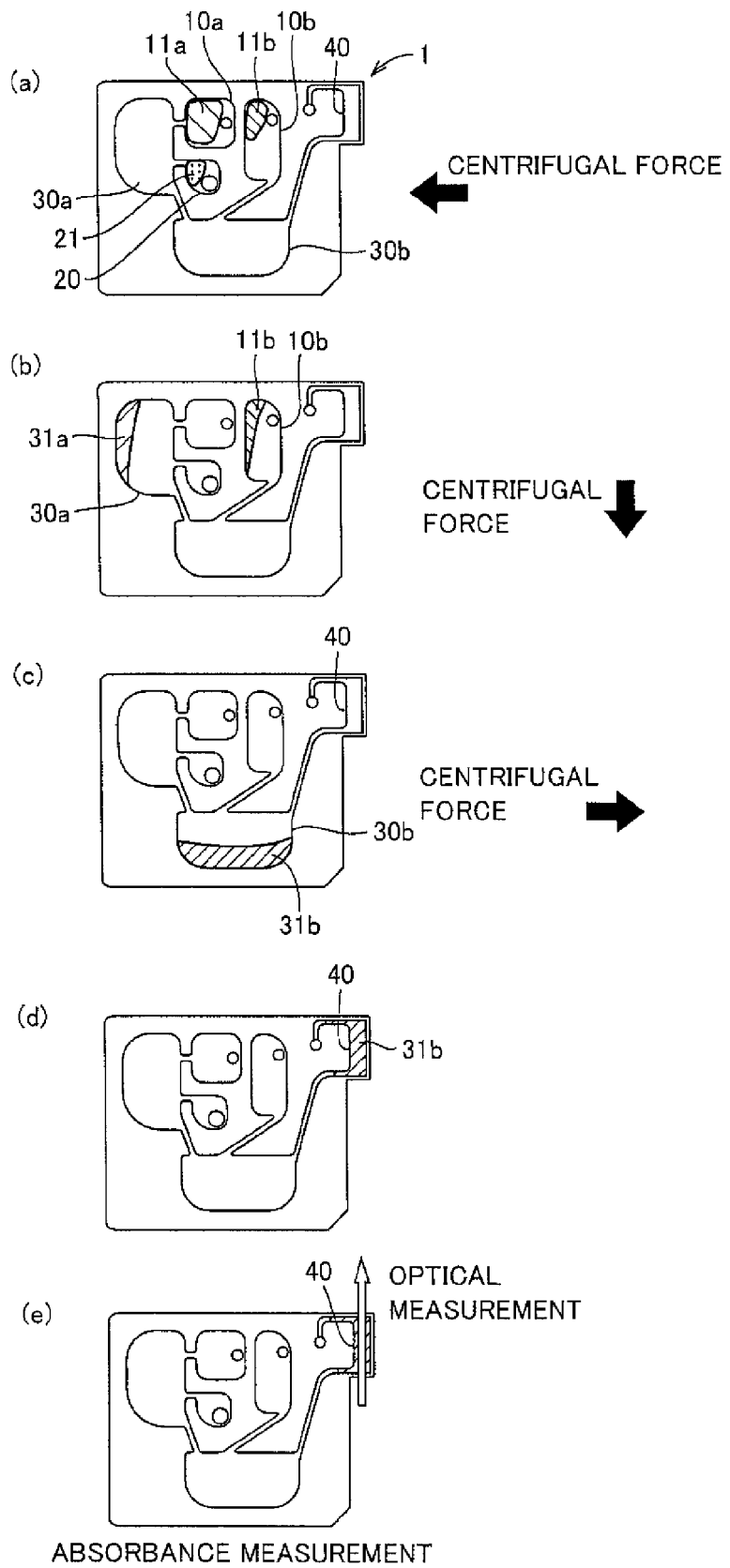
FIG. 9(a)-(e) is a schematic top view of a microchip in each step of a measurement method of Example 4.

First, a centrifugal force is applied leftward (in the direction of an arrow in FIG. 9(a)) to microchip 1 in a state as shown in FIG. 9(a). A test reagent 11a (a latex reagent on which an influenza A virus antibody is immobilized) that has been contained within a test reagent retaining portion 10a and sample 21 that has been introduced in a sample retaining portion 20 are thereby introduced into a mixing portion 30a and produce a liquid mixture 31a (FIG. 9(b)).

(2) Second Mixing Step

Sixty seconds after mixing test reagent 11a and sample 21 together, a centrifugal force is applied downward (in the direction of an arrow in FIG. 9(b)) to microchip 1 in a state as shown in FIG. 9(b). Liquid mixture 31a that has been introduced in mixing portion 30a and test reagent 11b (a gold colloid reagent on which an influenza B virus antibody is immobilized) that has been contained within test reagent retaining portion 10b are thereby introduced into a mixing portion 30b and produce a liquid mixture 31b (FIG. 9(c)).

(3) Introduction into Detecting Portion Step

Next, a centrifugal force is applied rightward (in the direction of an arrow in FIG. 9(c)). Liquid mixture 31b is thereby introduced into detecting portion 40 through a connecting flow channel (FIG. 9(d)).

(4) Detection Step

Liquid mixture 31b filled into the detecting portion undergoes optical measurement and is accordingly tested and/or analyzed. For instance, by applying light from the direction of an arrow shown in FIG. 9(e) and measuring the transmitted light, detection of a specific component in the liquid mixture, for example, is performed. In the present example, the absorbance for 505 nm wavelength light was measured.

Samples used in the present example were combined liquids of a nasal discharge from an influenza A affected individual or its diluted solution and a nasal discharge from an influenza B affected individual or its diluted solution.

As a test reagent for an object to be measured, namely an influenza A virus, a latex reagent on which an influenza A virus antibody was immobilized was used. As a test reagent for an influenza B virus, a gold colloid reagent on which an influenza B virus antibody was immobilized was used. The light used for measurement was of a wavelength of 505 nm, and each sample was measured once.

Figure 10:
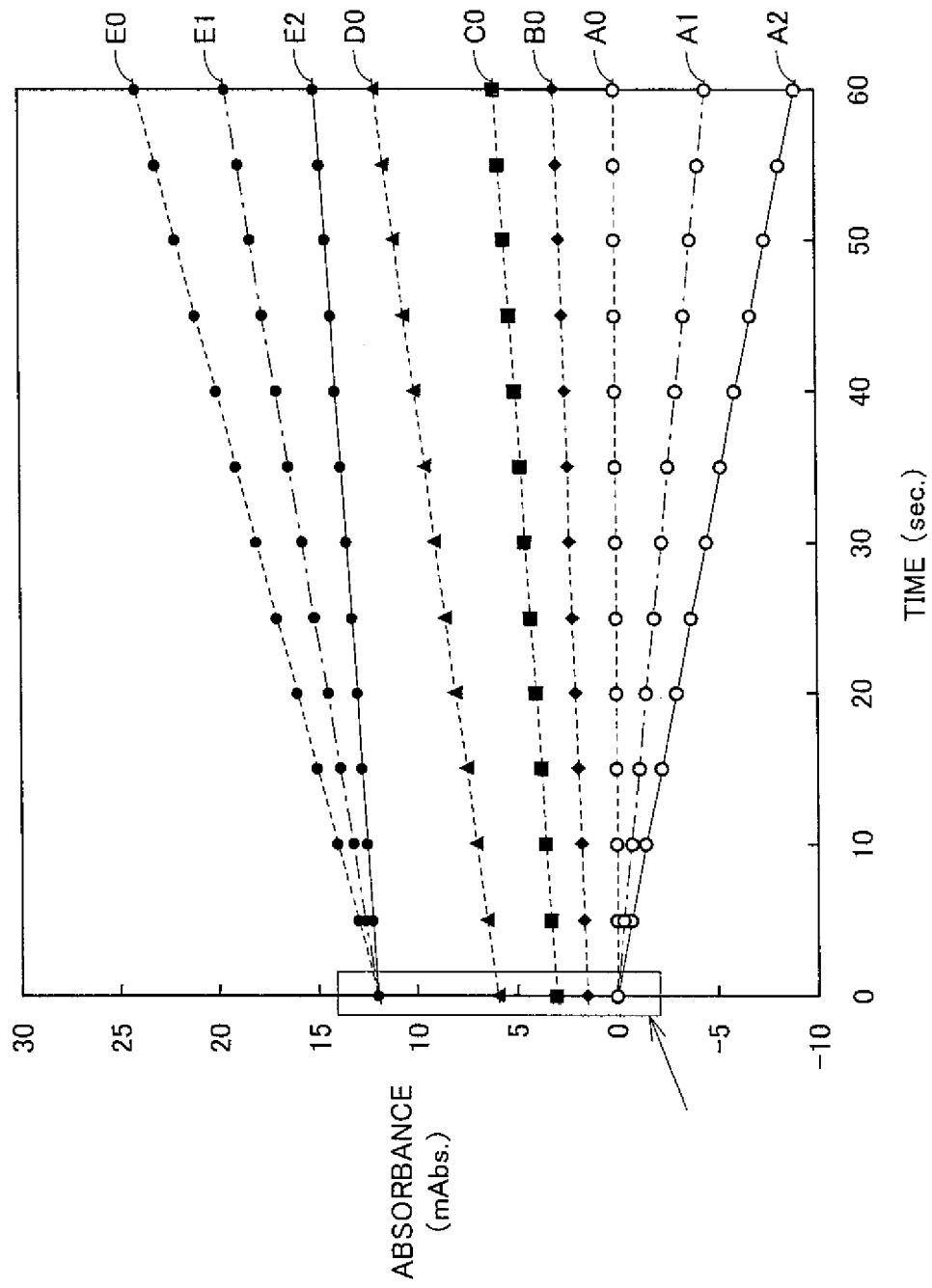
FIG. 10 is a graph showing measurements in Example 4.

The measurements are shown in FIG. 10. In FIG. 10, A0 is measurements solely for the nasal discharge from a healthy individual, A1 is measurements solely for a ½ diluted solution of the nasal discharge from an influenza B affected individual, and A2 is measurements solely for the nasal discharge from an influenza B affected individual. E0 is measurements solely for the nasal discharge from an influenza A affected individual, and D0, C0 and B0 are measurements solely for a ½ diluted solution, a ¼ diluted solution, a ⅛ diluted solution of the nasal discharge from an influenza A affected individual, respectively. E1 is measurements for a liquid mixture of equal parts of the nasal discharge from an influenza A affected individual and the nasal discharge from an influenza B affected individual.

Figure 11:
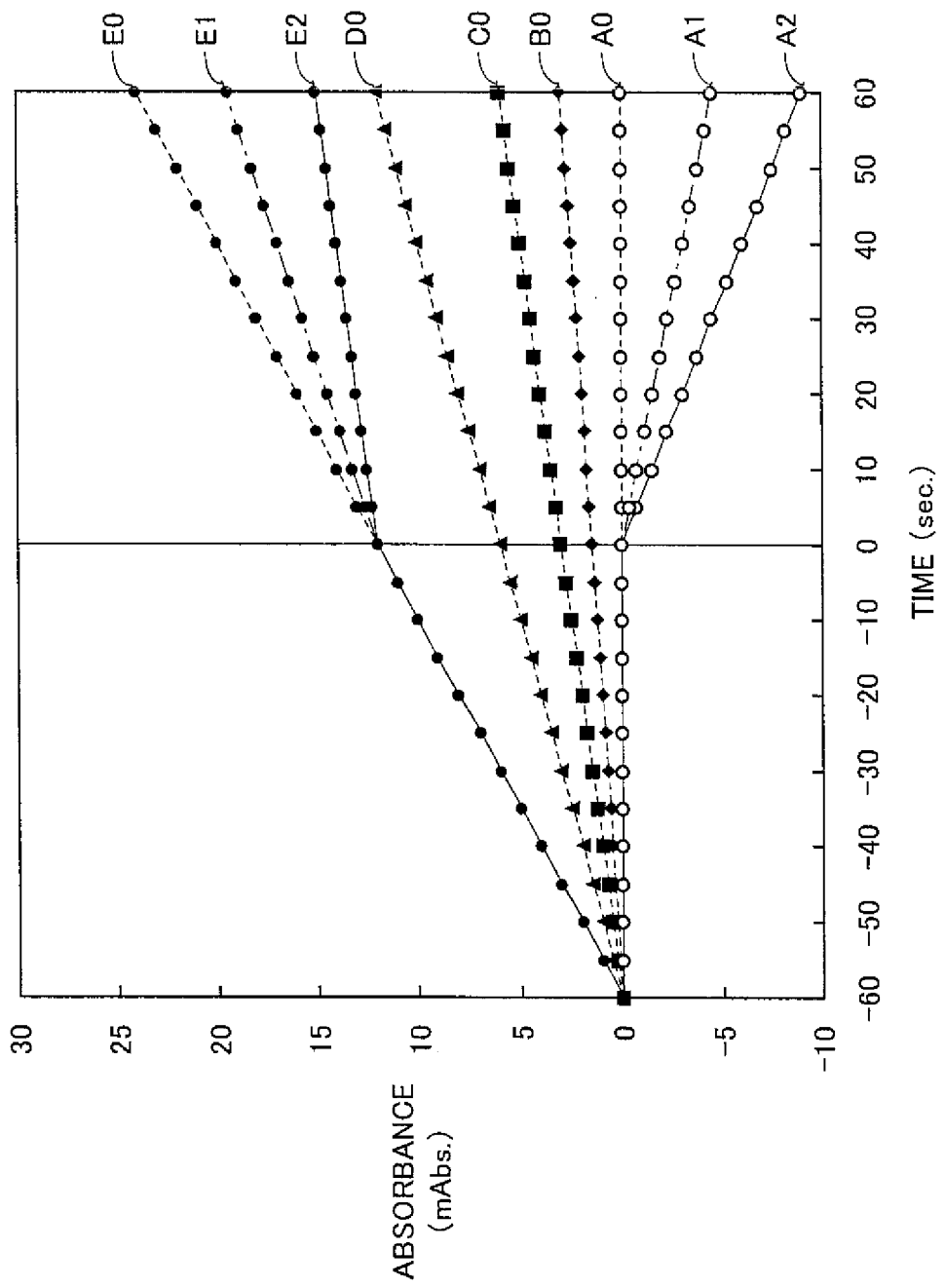
FIG. 11 is another graph showing the measurements in Example 4.

FIG. 11 is a graph extrapolating, from the measurements shown in FIG. 10, graphs for a time period from mixing of the latex reagent (test reagent 11a) to mixing of the gold colloid reagent (test reagent 11b). As can be seen from the above, it is possible to measure an influenza virus A based on the absorbance at time 0 in FIG. 10 (a section indicated by an allow in FIG. 10).

Figure 12:
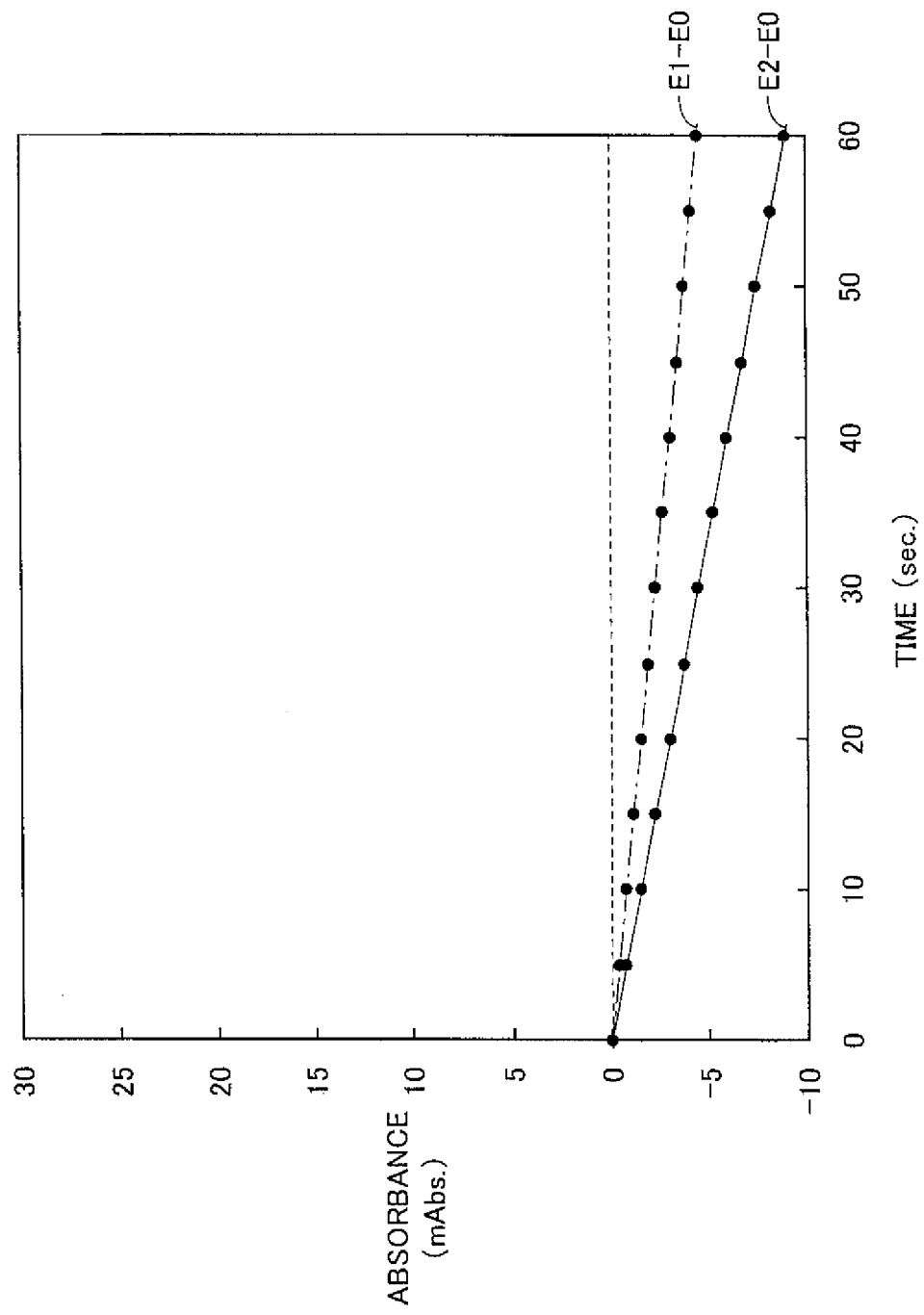
FIG. 12 is another graph showing measurements in Example 4.

In FIG. 12, "E1–E0" is a graph of values obtained by subtracting the absorbance of E0 from the absorbance of E1, which are shown in FIG. 10, while "E2–E0" is a graph of values obtained by subtracting the absorbance of E0 from the absorbance of E2, which are shown in FIG. 10. It can be seen that it is possible to measure an influenza B virus in this way.

Example 5

Figure 13:
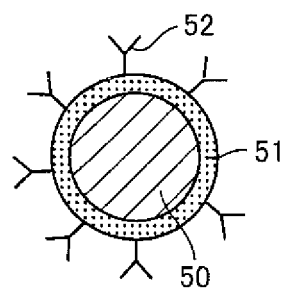
FIG. 13 is a schematic cross sectional view of a test reagent used in a measurement method of Example 5.

The present example uses, instead of the gold colloid reagent used in Example 1 (a liquid colloidal dispersion of a gold particle having a surface on which an influenza A virus antibody is immobilized), a liquid colloidal dispersion of a double-layer structured particle having a surface on which an antibody is immobilized as shown in FIG. 13. In FIG. 13, a core particle 50 composed of a material of a specific gravity of approximately 1 (such as a resin) has a surface on which a thin metal coating (metal layer) 51 is formed. Metal coating 51 has a surface on which an antibody 52 such as an influenza A virus antibody is immobilized.

Figure 14:
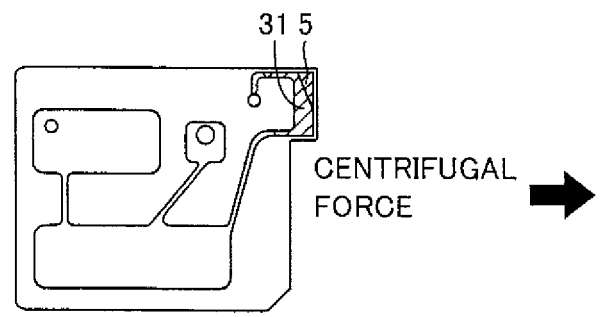
FIG. 14 is a schematic top view (prior art figure) for illustrating effects of a measurement method of Example 5.

In a microchip that performs a fluid treatment utilizing a centrifugal force, when a metal colloid reagent is used as a test reagent, since metal has a specific gravity (e.g., Au: 19.3, Pt: 21.45, Ag: 10.49) that is greater than the water's specific gravity of 1, application of a centrifugal force in the fluid treatment may cause metal 5 to separate in liquid mixture 31 containing a gold colloid reagent, as shown in FIG. 14.

In contrast, in the present example, the particle in the reagent is comparable to a core material 50 in specific gravity, and therefore it is possible to suppress the phenomenon in which application of a centrifugal force in a fluid treatment causes a particle on which an antibody is immobilized to separate in a liquid mixture within a biochip.

When a resin serves as the material having a specific gravity of approximately 1, core particle 50 composed of the resin can be readily controlled in particle size through various publicly-known methods, which makes it possible to provide enhanced measurement sensitivity. Examples of the resin include polyethylene (PE), polypropylene (PP), polystyrene (PS), an ABS resin, an AS resin, polycarbonate (PC), polyethylene terephthalate (PET), and polymethylpentene (PMP). Examples of metal coating 51 include gold, platinum, and silver.

It is noted that when a metal colloid reagent is used, measurement is performed utilizing surface plasmon resonance that is caused by an interaction between light and a free electron present on a metal surface. The metal colloid reagent in the present example, which has a free electron present on the surface of the metal coating, also exhibits a surface plasmon phenomenon, and therefore maintains a property required as a test reagent for in vitro diagnosis of an immunoreaction and the like. Accordingly, the metal colloid reagent in the present example has a desirable property of not exhibiting separation even when a centrifugal force is applied while maintaining a property as a test reagent, and can be suitably used in particular for a microchip performing a fluid treatment utilizing a centrifugal force.

It should be understood that the embodiments and examples disclosed herein are illustrative and non-restrictive in every respect. The scope of the present invention is defined by the terms of the claims rather than the above description, and is intended to include any modifications within the scope and meaning equivalent to the terms of the claims.

What is claimed is:

1. A measurement method for measuring a plurality of types of objects to be measured using a microchip, the method comprising:
    providing a microchip comprising:
        a reagent retaining portion; and
        a detecting portion, wherein
        said reagent retaining portion includes a plurality of types of test reagents corresponding respectively to said plurality of types of objects to be measured,
        the plurality of types of test reagents being such that a plurality of time courses for a change in detected values at said detecting portion caused by a reaction between each of said test reagents and a corresponding respective one of said objects to be measured are different from one other, wherein the time courses represent manners of change in the detected values over time,
    the method further comprising detecting whether the plurality of types of objects is contained in a sample by using the plurality of types of test reagents and a difference between the time courses for changes in detected values at said detection portion.

2. The measurement method according to claim 1, wherein said plurality of time courses include both a positive time course indicating the tendency of an increase in said detected value over time and a negative time course indicating the tendency of a decrease in said detected value over time.

3. The measurement method according to claim 1, wherein all of said plurality of time courses are time courses adapted to a rate assay in which said object to be measured is detected based on the rate of change in said detected value.

4. The measurement method according to claim 1, wherein said plurality of time courses include both a time course adapted to a rate assay in which said object to be measured is detected based on the rate of change in said detected value and a time course adapted to an end-point assay in which said object to be measured is detected based on an amount of change in said detected value relative to an initial value of said detected value.

5. The measurement method according to claim 1, wherein said plurality of types of test reagents include at least one type of latex reagent and at least one type of gold colloid reagent.

6. The measurement method according to claim 1, wherein
    said plurality of types of objects to be measured are an influenza A virus and an influenza B virus, and
    said plurality of types of test reagents are a latex reagent and a gold colloid reagent.

7. The measurement method according to claim 1, wherein said detected value is detected through optical measurement using a plurality of wavelengths.

8. A measurement method for measuring a plurality of types of objects to be
    measured using a microchip comprising:
        a sample retaining portion for retaining a sample;
        a reagent retaining portion for retaining a plurality of types of test reagents;
        a mixing portion for mixing said sample and said plurality of types of test reagents to produce a liquid mixture; and
        a detecting portion into which said liquid mixture is introduced, wherein the plurality of types of test reagents being such that a plurality of time courses for a change in detected values at said detecting portion caused by a reaction between each of said test reagents and a corresponding respective one of said objects to be measured are all different from one other; and
    wherein the time courses represent manners of change in the detected values over time, wherein the measurement method comprises:
        mixing said sample and said plurality of types of test reagents to produce a liquid mixture;
        introducing said liquid mixture into one said detecting portion; and
        determining whether each of said plurality of types of objects to be measured is contained in said sample depending on a time course for a change in detected value at one said detection portion.

9. The measurement method according to claim 8, wherein said detected values are changing due to transmittances of lights applied to said detection portion.

10. The measurement method according to claim 8, wherein said plurality of types of test reagents includes a test reagent whereby said detected value is increasing over time in the time course and a test reagent whereby said detected value is decreasing over time in the time course.

11. The measurement method according to claim 8, wherein said plurality of types of test reagents includes test reagents whereby reaction rates between each of said test reagents and a corresponding respective one of said objects to be measured are all different from each other.

\* \* \* \* \*